United States Patent
Ota et al.

(10) Patent No.: US 11,561,230 B2
(45) Date of Patent: Jan. 24, 2023

(54) REFERENCE STANDARD FOR BNP MEASUREMENT

(71) Applicant: SHIONOGI & CO., LTD., Osaka (JP)

(72) Inventors: Norio Ota, Toyonaka (JP); Keiichi Masuta, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 265 days.

(21) Appl. No.: 16/772,036

(22) PCT Filed: Dec. 28, 2018

(86) PCT No.: PCT/JP2018/048398
§ 371 (c)(1),
(2) Date: Jun. 11, 2020

(87) PCT Pub. No.: WO2019/131984
PCT Pub. Date: Jul. 4, 2019

(65) Prior Publication Data
US 2021/0172964 A1    Jun. 10, 2021

(30) Foreign Application Priority Data

Dec. 28, 2017 (JP) .............................. JP2017-254386

(51) Int. Cl.
*C07K 14/575* (2006.01)
*G01N 33/74* (2006.01)

(52) U.S. Cl.
CPC .......... *G01N 33/74* (2013.01); *C07K 14/575* (2013.01); *G01N 2333/58* (2013.01)

(58) Field of Classification Search
None
See application file for complete search history.

(56) References Cited

FOREIGN PATENT DOCUMENTS

| EP | 1 929 851 | 6/2008 |
|---|---|---|
| EP | 2 021 369 | 2/2009 |
| JP | 2009-510748 A | 3/2009 |
| JP | 2009-538288 A | 11/2009 |
| JP | 2010-535737 A | 11/2010 |
| JP | 2011-47829 A | 3/2011 |
| JP | 2014-32062 A | 2/2014 |
| JP | 6008645 B2 | 10/2016 |
| WO | WO 2006/029369 A2 | 3/2006 |
| WO | WO 2007/039355 A1 | 4/2007 |
| WO | WO 2007/138163 A2 | 12/2007 |
| WO | WO 2009/019236 A1 | 2/2009 |
| WO | WO 2017/210488 A1 | 12/2017 |

OTHER PUBLICATIONS

English translation of JP 2014032062 A, 2014, pp. 1-28.*
English translation of JP 6008645 B2, 2014, pp. 1-26.*
Cauliez, et al., "Cross-reactivity with endogenous proBNP from heart failure patients for three commercial BNP immunoassays", Clinica Chimica Acta, vol. 413, 2012, pp. 337-338.
Clerico et al., "State of the art of BNP and NT-proBNP immunoassays: The CardioOrmoCheck study", Clinica Chimica Acta, vol. 414, 2012, pp. 112-119 (Total No. pp. 9).
International Search Report issued in PCT/JP2018/048398 (PCT/ISA/210), dated Mar. 19, 2019.
Kono et al., "An Immunoradiometric Assay for Brain Natriuretic Peptide in Human Plasma", The Japanese Journal of Nuclear Medicine Technology, vol. 13, No. 1, 1993, pp. 2-7.
Luckenbill et al., "Cross-Reactivity of BNP, NT-proBNP, and proBNP in Commercial BNP and NT-proBNP Assays: Preliminary Observations from the IFCC Committee for Standardization of Markers of Cardiac Damage", Clinical Chemistry, vol. 54, No. 3, 2008, pp. 619-620 (Total No. pp. 3).
Prontera et al., "Proficiency testing project for brain natriuretic peptide (BNP) and the N-terminal part of the propeptide of BNP (NT-proBNP) immunoassays: the CardioOrmocheck study", Clinical Chemistry and Laboratory Medicine, vol. 47, No. 6, 2009, pp. 762-768.
Saenger et al., "Specificity of B-Type Natriuretic Peptide Assays: Cross-Reactivity with Different BNP, NT-proBNP, and proBNP Peptides", Clinical Chemistry, vol. 63, No. 1, 2017, pp. 351-358.
Semenov et al., "Searching for a BNP standard: Glycosylated proBNP as a common calibrator enables improved comparability of commercial BNP immunoassays", Clinical Biochemistry, vol. 50, 2017, pp. 181-185.

(Continued)

*Primary Examiner* — Elizabeth C. Kemmerer
(74) *Attorney, Agent, or Firm* — Birch, Stewart, Kolasch & Birch, LLP

(57) ABSTRACT

A reference standard set for BNP measurement, including a plurality of reference standards including BNP-32 and proBNP, wherein the ratio BNP-32/proBNP (mole ratio) differs between the reference standards, and when a reference standard having a high mole ratio and a reference standard having a low mole ratio are compared, the BNP concentration, which is the sum total of the BNP-32 concentration and the proBNP concentration, is lower in the reference standard having a high mole ratio than in the reference standard having a low mole ratio. The present invention makes it possible to provide: a reference standard set for BNP measurement, whereby, when the BNP concentration value of a specimen measured by a certain BNP measurement method and the BNP concentration value of the specimen measured by another BNP measurement method are corrected using the reference standard set for BNP measurement, the corrected measurement values can be made to more closely coincide in comparison with a case in which the measurement values are corrected using a conventional reference standard; and a method for correcting, using the reference standard set for BNP measurement, the measured BNP concentration value of a specimen.

7 Claims, 11 Drawing Sheets

Specification includes a Sequence Listing.

(56) References Cited

OTHER PUBLICATIONS

Written Opinion of the International Searching Authoriy issued in PCT/JP2018/048398 (PCT/ISA/237), dated Mar. 19, 2019.
English translation of International Preliminary Report on Patentability and Written Opinion dated Jul. 9, 2020, in PCT/JP2018/048398 (Forms PCT/IB/338,PCT/B/373, and PCT/ISA/237).

* cited by examiner

REFERENCE STANDARD FOR BNP MEASUREMENT

TECHNICAL FIELD

The present invention relates to a reference standard set for BNP measurement and a method for correcting, by using this set, a BNP concentration value measured in a sample.

BACKGROUND ART

BNP (brain natriuretic peptide) is a hormone eliciting vasodilator action and diuretic and natriuretic effects and regulates sympathetic nerve system and renin-aldosterone system.

BNP is primarily secreted from a cardiac ventricle when a load is applied on the heart. The plasma BNP concentration (the sum value of proBNP and BNP-32) in healthy subjects is very low and is significantly increased depending on the severity of chronic or acute cardiac failure in patients. Thus, measuring the plasma BNP concentration is considered to be useful in understanding pathology of heart disease including heart failure.

The BNP gene is transcribed and translated into BNP as a preproBNP precursor. A signal peptide is cleaved therefrom to produce proBNP (proBNP1-108) as a BNP-32 precursor, which is then cleaved to generate N-terminal proBNP (proBNP1-76) and biologically active BNP-32 (proBNP77-108).

The proBNP and BNP-32 are present at a certain ratio in blood. Here, BNP assay kits for diagnosing heart disease are to measure the sum value of proBNP and BNP-32 as a measured BNP concentration value. These assay kits have been widely used for diagnosis of, for instance, heart disease.

[Chemical Formula 1]

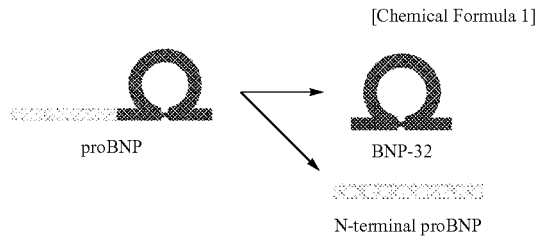

Different BNP assay kits may reportedly cause a deviation in the plasma BNP concentration between the BNP assay kits when the same sample is measured (Non-patent Documents 1 and 2). Essentially, the deviation in the plasma BNP concentration value measured in the same sample should be minimum between the different BNP assay kits. For instance, a patient with heart disease may be transferred between medical institutions visited and these medical institutions before and after the transfer may use different BNP assay kits. In this case, it is desirable to minimize the difference in the plasma BNP concentration value measured between the BNP assay kits to determine precisely how pathological conditions of the heart disease change and be able to determine therapeutic effects.

Standards for drawing a standard curve as included in commercially available typical BNP assay kits are each composed of BNP-32 alone. Non-patent Document 3 indicates a method using proBNP as a BNP assay standard.

Meanwhile, Patent Document 1 discloses a method using, as a standard for calibration between BNP assay kits, a mixture of proBNP and BNP-32 at a simple mixing ratio of from 6:4 to 4:6 (a mole ratio).

PRIOR ART REFERENCES

Patent Document

[Patent Document 1] Japanese Patent No. 6008645

Non-Patent Document

[Non-patent Document 1] Clin Chem Lab Med (2009) 47(6): 762-768
[Non-patent Document 2] Clinica Chimica Acta (2012) 414: 112-119
[Non-patent Document 3] Clinical Biochemistry (2017) 50: 181-185
[Non-patent Document 4] "Kaku Igaku Gijutu (Nuclear Medicine Technology)" (1993) 13: 2-7

SUMMARY OF THE INVENTION

Problems to be Solved by the Invention

Meanwhile, an additive ratio of proBNP and BNP-32 in standards in the above conventional art does not correctly reflect an abundance ratio of proBNP and BNP-32 in actual patients with heart disease. Thus, even when the standards indicated by the above conventional art are used, there has been a variation in the value measured in an actual sample among BNP assay kits.

The present invention addresses the problem of providing: a BNP assay standard set such that when the BNP assay standard set is used to correct a BNP concentration value measured in a sample by a certain BNP assay and a BNP concentration value measured in the sample by another BNP assay, the post-correction measured values can be matched better than when the above measured values are corrected using a conventional standard; and a method for correcting, by using the BNP assay standard set, a BNP concentration value measured in a sample.

Means for Solving the Problem

The present inventors have investigated how the BNP concentration is related with the abundance ratio of proBNP in many samples so as to precisely grasp the abundance ratio of proBNP and BNP-32 in actual patients with heart disease. As a result, it has been found that BNP concentrations cause different abundance ratios of proBNP. This finding has been utilized to complete the invention using a BNP assay standard set including: a standard at a high BNP-32/proBNP mole ratio as a standard with a low BNP concentration; and a standard at a low BNP-32/proBNP mole ratio as a standard with a high BNP concentration.

Specifically, the invention is summarized as follows.

[1] A BNP assay standard set comprising a plurality of standards, each containing BNP-32 and proBNP, wherein BNP-32/proBNP (a mole ratio) differs among the standards; and when the standard at a high mole ratio and the standard at a low mole ratio are compared with each other, the standard at a high mole ratio has a lower BNP concentration that is the sum value of BNP-32 and proBNP concentrations than the standard at a low mole ratio.

[2] The BNP assay standard set according to [1], wherein the set comprises at least two standards, wherein the mole ratio (BNP-32/proBNP) of a first standard is from 40/60 to 60/40, and the mole ratio (BNP-32/proBNP) of a second standard is from 15/85 to 35/65.

[3] The BNP assay standard set according to [2], wherein the first standard has a BNP concentration of from 20 to 75 pg/mL and the second standard has a BNP concentration of from 150 to 300 pg/mL.

[4] A BNP assay kit comprising the BNP assay standard set according to any one of [1] to [3].

[5] A BNP assay kit comprising information about a correction factor determined using the BNP assay standard set according to any one of [1] to [3].

[6] A method for measuring a BNP concentration in a sample, comprising using the BNP assay standard set according to any one of [1] to [3].

[7] A method for correcting a BNP concentration value measured in a sample, comprising using the BNP assay standard set according to any one of [1] to [3].

[8] The method according to [7], further comprising the following steps (A) and (B):

(A) using the plurality of standards to determine a correction factor between a BNP concentration value measured by a standard BNP assay procedure and a BNP concentration value measured by the BNP assay to be corrected, for each of ranges of BNP concentration values measured by a BNP assay to be corrected; and (B) using the correction factor to correct the BNP concentration value measured in the sample by the BNP assay to be corrected.

[9] The method according to [7], further comprising the following steps (1) to (3):

(1) using both a reference BNP assay and a BNP assay to be corrected to measure BNP concentrations in both a first standard and a second standard;

(2) determining, for each of the first standard and the second standard, the following ratio:

[a BNP concentration value measured by the reference BNP assay]/[a BNP concentration value measured by the BNP assay to be corrected] to determine the ratio for the first standard as a first correction factor and the ratio for the second standard as a second correction factor;

(3) correcting, based on the first correction factor and the second correction factor, an actual measured value being a BNP concentration value measured in a sample by the BNP assay to be corrected to the following numerical value:

(i) when the actual measured value is less than or equal to the BNP concentration value of the first standard as measured by the BNP assay to be corrected, a numerical value obtained by multiplying the actual measured value by the first correction factor;

(ii) when the actual measured value is more than the BNP concentration value of the first standard as measured by the BNP assay to be corrected and less than or equal to the BNP concentration value of the second standard as measured by the BNP assay to be corrected, a numerical value obtained by multiplying the actual measured value by a correction factor determined by the following formula:

the first correction factor+[(the second correction factor−the first correction factor)/(the BNP concentration value of the second standard as measured by the BNP assay to be corrected−the BNP concentration value of the first standard as measured by the BNP assay to be corrected)]× (the actual measured value−the BNP concentration value of the first standard as measured by the BNP assay to be corrected); or (iii) when the actual measured value is more than the BNP concentration value of the second standard as measured by the BNP assay to be corrected, a numerical value obtained by multiplying the actual measured value by the second correction factor.

Effect of the Invention

The present invention can provide: a BNP assay standard set such that when the BNP assay standard set is used to correct a BNP concentration value measured in a sample by a certain BNP assay and a BNP concentration value measured in the sample by another BNP assay, the post-correction measured values can be matched better than when the above measured values are corrected using a conventional standard; and a method for correcting, by using the BNP assay standard set, a BNP concentration value measured in a sample.

MODE FOR CARRYING OUT THE INVENTION

Figure 1A:
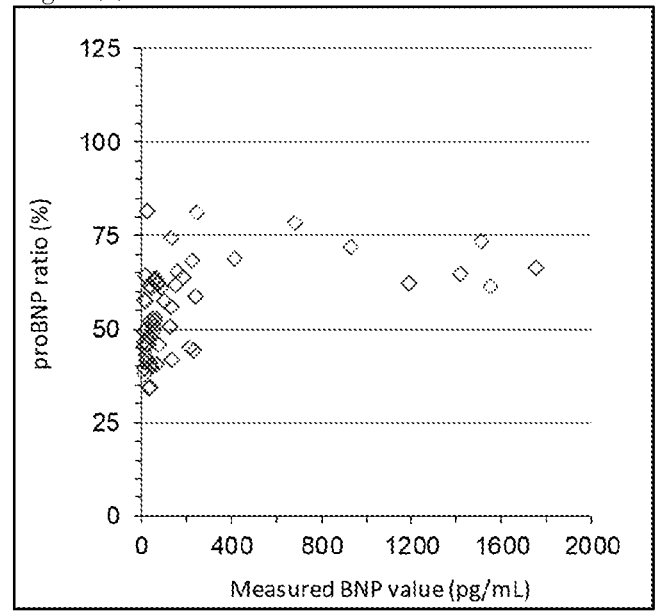
FIG. 1(a) shows the relationship between the abundance ratio of proBNP and the measured BNP concentration value over the entire assay range as measured in Example 1-1.

The present invention provides a BNP assay standard set comprising a plurality of standards, each containing BNP-32 and proBNP.

The BNP assay standard set is applicable to correction of a BNP concentration value measured by a BNP assay. In addition, the BNP assay standard set may be used to draw a standard curve, which is then used to optionally measure the BNP concentration in a sample.

As used herein, the "proBNP" means proBNP1-108, which consists of 108 amino acid residues (SEQ ID NO: 1) and has a molecular weight of about 12 KD. The proBNP may be readily prepared in accordance with a known procedure and may be expressed, for instance, in E. coli as a recombinant proBNP. Also, the "proBNP" is optionally glycosylated proBNP. For instance, the glycosylated proBNP with a molecular weight of about 35 KD may be produced by expressing in HEK293 cells in accordance with a known procedure. Note that the proBNP may be a synthetic one.

As used herein, the "BNP-32" means proBNP77-108, which consists of 32 amino acid residues (SEQ ID NO: 2) and has a molecular weight of about 3.5 KD. The BNP-32 may be readily synthesized in accordance with a known procedure. Note that the BNP-32 is optionally a recombinant.

As used herein, the term "plurality of" refers to an integer of 2 or larger and may mean 2, 3, 4, 5, 6, 7, or 8, at least 2, at least 3, at least 4, at least 5, at least 6, at least 7, or at least 8.

As used herein, the "standard" means each individual standard included in the BNP assay standard set, and a combination of a plurality of standards is used as the BNP assay standard set. Each standard contains BNP-32 and proBNP. The standard may be referred to as, for instance, a first standard, a second standard, a third standard, a fourth standard, or a fifth standard or, for instance, a BNP assay standard for measurement in a low-concentration range or a BNP assay standard for measurement in a high-concentration range. When the standard is herein designated as, for instance, a first standard, a second standard, a third standard, a fourth standard, or a fifth standard, the BNP concentration is indicated to increase as the ordinal number becomes larger.

In the invention, the BNP-32/proBNP (mole ratio) varies between the standards. In addition, when a standard at a high mole ratio and a standard at a low mole ratio are compared between the two standards, the standard at a high mole ratio has a lower BNP concentration than the standard at a low mole ratio. The mole ratio in the case of the first standard is preferably from 40/60 to 60/40 and more preferably 45/55 to 55/45 (each indicating BNP-32/proBNP). The mole ratio in the case of the second standard is preferably from 15/85 to 35/65 and more preferably from 20/80 to 30/70 (each indicating BNP-32/proBNP).

The BNP concentration of the first standard is preferably from 20 to 75 pg/mL, more preferably from 25 to 60 pg/mL, and still more preferably from 30 to 50 pg/mL. In addition, the BNP concentration of the second standard is preferably from 150 to 300 pg/mL, more preferably from 160 to 250 pg/mL, and still more preferably from 180 to 220 pg/mL. The "BNP concentration" herein means the sum value of BNP-32 and proBNP concentrations. When the BNP concentration is mass concentration, it is expressed as the sum value of the BNP-32 concentration and the proBNP concentration as a BNP-32 equivalent.

Each standard included in the BNP assay standard set may be prepared by various procedures.

Purified products of BNP-32 and proBNP may be added to prepare a standard. In this case, based on the substance amounts (mol) of proBNP and BNP-32 added, the BNP concentration and the BNP-32/proBNP (mole ratio) of the standard are specified. In the case of a purified product containing BNP-32 and proBNP, the standard may be prepared by diluting them, if appropriate, on the basis of the molarity of each of proBNP or BNP-32 as measured using amino acid analysis, absorbance measurement method, dye-binding assay, chromatography, electrophoresis, and the like.

Preferably, the standard may be used after the BNP-32 and proBNP prepared, as described above, are mixed and then diluted with a suitable diluent or concentrated to adjust, if appropriate, the BNP-32/proBNP mole ratio and the BNP concentration. Further, the BNP-32 and proBNP prepared, as described above, are lyophilized. Then, when used, a diluent may be added thereto for usage.

Examples of the diluent for a standard may include plasma from a healthy subject(s) or buffers (e.g., phosphate buffer, imidazole buffer, triethanolamine-hydrochloric acid, citrate buffer, and Good's buffer), and the diluent may contain, for instance, a protein stabilizer (e.g., bovine serum albumin (BSA)), a protease inhibitor (e.g., aprotinin), sodium chloride, and a preservative (e.g., sodium azide, ProClin, and an antibiotic). As the diluent, it is preferable to use plasma from a healthy subject. The plasma is preferably free of BNP (e.g., proBNP or BNP-32). For instance, plasma from a healthy subject without heart disease is usually substantially free of BNP and is thus preferable. It is possible to use, as the diluent, human plasma from which BNP has been removed. Examples of the procedure for removing BNP include a method including reacting, for a certain period, human plasma and, for instance, polystyrene beads having immobilized an antibody (e.g., BC203, KY-hBNP-II) that recognizes a common epitope between proBNP and BNP-32.

An embodiment of the invention can provide a BNP assay kit including the above BNP assay standard set.

In an embodiment of the invention, the above BNP assay standard set may be included as a component of a BNP assay kit. Any BNP assay kit may be herein allowed as long as the kit is used to measure a BNP concentration. Examples thereof may include a BNP measurement kit using an immunoradiometric assay (IRMA) (Non-patent Document 4), MI02 Shionogi BNP (Shionogi & Co., Ltd.), ARCHITECT BNP-JP (Abbott Japan), PATHFAST BNP (LSI Medience Corporation), Determiner CL-BNP (Kyowa Medics), ADVIA Centaur BNP assay (Siemens Healthcare diagnostics), Rapidchip BNP (SEKISUI MEDICAL CO., LTD.), E-test "TOSOH" II (BNP) (TOSOH CORPORATION), Lumipulse BNP (FUJIREBIO Inc.), Triage BNP Test (Alere), and i-STAT BNP Test (Abbott POC).

The above BNP assay kits may be used for assisting in heart failure diagnosis, determining therapeutic effects on heart disease, screening for heart disease, or the like.

As used herein, the "heart disease" has the broadest meaning used in the art, and is a general term of disease including: heart failure, which refers to a syndrome caused by failure of heart function to pump a sufficient amount of blood in circulation and includes a decrease in cardiac output and an increase in venous pressure accompanied by it, and the resulting various clinical conditions; arrhythmia (atrial fibrillation, ventricular fibrillation, and the like); and hypertension. Examples of a cause for the heart failure can include valvular heart disease, ischemic heart disease, congenital heart disease, dilated cardiomyopathy, hypertrophic cardiomyopathy, atrial septal defect, ventricular septal defect, and symptomatic heart disease.

As used herein, the "assisting in diagnosis" refers to providing information about heart disease diagnosis in which the BNP assay kit is used alone or in combination with an additional test, or the like. Examples of the additional test(s) may include electrocardiography, echocardiography, cardiac catheterization, a blood test other than a BNP assay, blood pressure measurement, and an interview.

An embodiment of the invention can provide a method for measuring a BNP concentration in a sample, including using the above BNP assay standard set.

As used herein, the "measured BNP concentration value" refers to a BNP concentration value measured using a BNP assay kit. With regard to the "measured BNP concentration value" and the "BNP concentration" (the sum value of concentrations of BNP-32 and proBNP actually included in a sample), the "BNP concentration" in the same sample is identical. However, regarding the "BNP concentration value measured" in the same sample by using each assay kit, the numerical value may deviate because compatibility with BNP-32 and proBNP differs between the assay kits, different standards are used in the respective BNP assay kits, and/or the abundance ratio of proBNP and BNP-32 varies depending on a sample.

As used herein, the "correction" refers to converting the BNP concentration value measured in a sample by a BNP assay to be corrected to an equivalent of the BNP concentration value measured in the sample by a reference BNP assay. Preferably, the term refers to multiplying, by the below-described correction factor, the BNP concentration value measured in a sample by a BNP assay to be corrected.

An embodiment of the invention can provide a method for correcting a BNP concentration value measured in a sample, including using the above BNP assay standard set.

Examples of the sample may include a biological specimen (e.g., blood, plasma, serum, cerebral fluid, lymph, pericardial effusion, tissue, cells, or urine). Preferred is blood or plasma. The sample may be preferably derived from a human.

A method according to an embodiment of the invention may include the following steps (A) and (B).

In an embodiment of the invention, step (A) may be a step of using the plurality of standards to determine a correction factor between a BNP concentration value measured by a reference BNP assay and a BNP concentration value measured by the BNP assay to be corrected, for each of ranges of BNP concentration values measured by a BNP assay to be corrected.

The "reference BNP assay" is not particularly limited as long as the BNP assay can be used to detect a common epitope between BNP-32 and proBNP to quantify both the BNP-32 and proBNP. The assay may be an immunoradiometric assay (IRMA), a fluorescence immunoassay (FIA), or a chemiluminescence enzyme immunoassay (CLEIA). Each assay may be herein referred to as a "standard assay procedure". The reference BNP assay is herein used to measure a BNP concentration. Meanwhile, an assay widely recognized as an assay having high diagnosis and evaluation accuracy is usually adopted as the reference method. The assay protocol and conditions for IRMA can be as described in Non-patent Document 4. Regarding a fluorescence immunoassay (FIA) or a chemiluminescence enzyme immunoassay (CLEIA), a measurement procedure and conditions known may be used.

The "BNP assay to be corrected" is not particularly limited as long as the BNP assay can be used to detect a common epitope between BNP-32 and proBNP to quantify both the BNP-32 and proBNP. Examples may include a chemiluminescence enzyme immunoassay (CLEIA) (e.g., an assay using MI02 Shionogi BNP (Shionogi & Co., Ltd.), an assay using PATHFAST BNP (LSI Medience Corporation), an assay using Determiner CL-BNP (Kyowa Medics), or an assay using Lumipulse BNP (FUJIREBIO Inc.)), a chemiluminescence immunoassay (CLIA) (e.g., an assay using ARCHITECT BNP-JP (Abbott Japan), or an assay using ADVIA Centaur BNP assay (Siemens Healthcare Diagnostics), a fluorescent enzyme immunoassay (FEIA) (e.g., an assay using E-test "TOSOH" II (BNP) (TOSOH CORPORATION)), a fluorescence immunoassay (FIA) (e.g., an assay using Triage BNP Test (Alere)), immunochromatography (e.g., Rapidchip BNP (SEKISUI MEDICAL CO., LTD.)), an enzyme immunoassay (EIA) (e.g., an assay using i-STAT BNP Test (Abbott POC)), an electrochemical luminescence immunoassay (ECLIA), an enzyme-linked immunosorbent assay (ELISA), a radioimmunoassay (RIA), and an immunoagglutination test. The BNP assay to be corrected may be herein used to obtain a BNP concentration value measured. An assay protocol and conditions known may be used as an assay protocol and conditions for each assay. Regarding the above-described kits, it is possible to use an assay protocol and conditions described in a package insert of each kit.

As used herein, the "correction factor" refers to a factor for converting the BNP concentration value measured in a sample by a BNP assay to be corrected to an equivalent of the BNP concentration value measured in the sample by a reference BNP assay. Preferably, the term refers to a factor for converting the BNP concentration value measured in a sample by a BNP assay to be corrected to an equivalent of the BNP concentration value measured in the sample by a reference BNP assay after the former BNP concentration value is multiplied by this correction factor.

Both a reference BNP assay and a BNP assay to be corrected are used to measure BNP concentrations of respective standards to determine a correction factor regarding the respective standards by using the following formula:

[a BNP concentration value measured by the reference BNP assay]/[a BNP concentration value measured by the BNP assay to be corrected].

The correction factor for a BNP concentration value (actual measured value) measured in a sample by a BNP assay to be corrected is determined by linear interpolation based on correction factors, regarding two standards, for the BNP concentration value measured by the BNP assay to be corrected, which the actual measured value is put between numerical values with the minimum difference (including a case where the actual measured value is equal to the measured BNP concentration value of the high level standard) as well as BNP concentration values of these standards as measured by the BNP assay to be corrected. In addition, when the actual measured value is less than or equal to the BNP concentration value of a first standard as measured by the BNP assay to be corrected, the correction factor regarding the first standard is a correction factor for the actual measured value. When the actual measured value is more than the BNP concentration value of a standard with the largest BNP concentration as measured by the BNP assay to be corrected, the correction factor regarding this standard is a correction factor for the actual measured value.

The "range of the BNP concentration value measured" is determined depending on the BNP concentration values of the respective standards as measured by the BNP assay to be corrected. For instance, when the first standard and the second standard are used for correction, the measured BNP concentration values of the respective standards are set to boundary values of the range. Each range determined includes a range from 0 pg/mL to the measured BNP concentration value of the first standard, a range from the measured BNP concentration value of the first standard to the measured BNP concentration value of the second standard, or a range from the measured BNP concentration value of the second standard to a higher measured BNP concentration value. It is preferable that the BNP concentration of each standard may be set to a boundary value of the range. Examples thereof may include 0 to 20 pg/mL, 20 to 150 pg/mL, 150 to 2000 pg/mL, 0 to 75 pg/mL, 75 to 300 pg/mL, 300 to 2000 pg/mL, 0 to 25 pg/mL, 25 to 160 pg/mL, 160 to 2000 pg/mL, 0 to 60 pg/mL, 60 to 240 pg/mL, 240 to 2000 pg/mL, 0 to 30 pg/mL, 30 to 180 pg/mL, 180 to 2000 pg/mL, 0 to 50 pg/mL, 50 to 220 pg/mL, 220 to 2000 pg/mL, or 0 to 40 pg/mL, 40 to 200 pg/mL, and 200 to 2000 pg/mL.

In an embodiment of the invention, step (B) may be a step of using the correction factor to correct the BNP concentration value measured in the sample by the BNP assay to be corrected.

A method according to an embodiment of the invention may include the following steps (1) to (3).

In an embodiment of the invention, step (1) may be a step of using both a reference BNP assay and a BNP assay to be corrected to measure BNP concentrations of both a first standard and a second standard.

In an embodiment of the invention, step (2) may be a step of determining, for each of the first standard and the second standard, the following ratio:

[a BNP concentration value measured by the reference BNP assay]/[a BNP concentration value measured by the BNP assay to be corrected]

to determine the ratio for the first standard as a first correction factor and the ratio for the second standard as a second correction factor.

In an embodiment of the invention, step (3) may be a step of correcting, based on the first correction factor and the second correction factor, an actual measured value being a BNP concentration value measured in a sample by the BNP assay to be corrected to the following numerical value:

(i) when the actual measured value is less than or equal to the BNP concentration value of the first standard as measured by the BNP assay to be corrected, a numerical value obtained by multiplying the actual measured value by the first correction factor;

(ii) when the actual measured value is more than the BNP concentration value of the first standard as measured by the BNP assay to be corrected and less than or equal to the BNP concentration value of the second standard as measured by the BNP assay to be corrected, a numerical value obtained by multiplying the actual measured value by a correction factor determined by the following formula:

the first correction factor+[(the second correction factor−the first correction factor)/(the BNP concentration value of the second standard as measured by the BNP assay to be corrected−the BNP concentration value of the first standard as measured by the BNP assay to be corrected)]× (the actual measured value−the BNP concentration value of the first standard as measured by the BNP assay to be corrected); or (iii) when the actual measured value is more than the BNP concentration value of the second standard as measured by the BNP assay to be corrected, a numerical value obtained by multiplying the actual measured value by the second correction factor.

As used herein, the "actual measured value" refers to a BNP concentration value measured in a sample by a BNP assay to be corrected.

Based on the corrected numerical values, a standard curve may be drawn. This standard curve can be used to obtain a BNP concentration included in a sample from the BNP concentration value measured in the sample. In addition, this standard curve may be included in a package insert of a BNP assay kit. Further, information about the BNP concentration obtained from the standard curve may be utilized for assisting in the diagnosis.

An embodiment of the invention can provide a BNP assay kit including information about a correction factor estimated using the BNP assay standard set.

The "information about a correction factor estimated using the BNP assay standard set" herein refers to information including correction factors estimated using the BNP assay standard set, a correction method, and a standard curve prepared on the basis of the corrected numerical values. This information may be used to correct the BNP concentration value measured in a sample by the BNP assay to be corrected. The above information may be provided through a medium including the information, and may be provided using, for instance, a written document or an electronic medium or may be provided using an identifier such as bar code or QR code.

In a method according to an embodiment of the invention, not only the first standard and the second standard, but also a third standard, a fourth standard, and a fifth standard, for instance, may be used. In this case, in addition to the first correction factor and the second correction factor, it is possible to use, for instance, a third correction factor, a fourth correction factor, and a fifth correction factor corresponding to the third standard, the fourth standard, and the fifth standard, respectively.

For instance, when the first to $n^{th}$ standards are used (where n is an integer of 3 or more), step (3) may be the following step (3) of correcting, based on the first correction factor to the $n^{th}$ correction factor, an actual measured value being a BNP concentration value measured in a sample by the BNP assay to be corrected to the following numerical value:

(i) when the actual measured value is less than or equal to the BNP concentration value of the first standard as measured by the BNP assay to be corrected, a numerical value obtained by multiplying the actual measured value by the first correction factor;

(ii) when the actual measured value is more than the BNP concentration value of the first standard as measured by the BNP assay to be corrected and less than or equal to the BNP concentration value of the second standard as measured by the BNP assay to be corrected, a numerical value obtained by multiplying the actual measured value by a correction factor determined by the following formula:

the first correction factor+[(the second correction factor−the first correction factor)/(the BNP concentration value of the second standard as measured by the BNP assay to be corrected−the BNP concentration value of the first standard as measured by the BNP assay to be corrected)]× (the actual measured value−the BNP concentration value of the first standard as measured by the BNP assay to be corrected); or (iii) when the actual measured value is more than the BNP concentration value of the second standard as measured by the BNP assay to be corrected and less than or equal to the BNP concentration value of the third standard as measured by the BNP assay to be corrected, a numerical value obtained by multiplying the actual measured value by a correction factor determined by the following formula:

the second correction factor+[(the third correction factor−the second correction factor)/(the BNP concentration value of the third standard as measured by the BNP assay to be corrected−the BNP concentration value of the second standard as measured by the BNP assay to be corrected)]×(the actual measured value−the BNP concentration value of the second standard as measured by the BNP assay to be corrected); or (i×n) when the actual measured value is more than the BNP concentration value of the $(n-1)^{th}$ standard as measured by the BNP assay to be corrected and less than or equal to the BNP concentration value of the $n^{th}$ standard as measured by the BNP assay to be corrected, a numerical value obtained by multiplying the actual measured value by a correction factor determined by the following formula:

the $(n-1)^{th}$ correction factor+[(the $n^{th}$ correction factor−the $(n-1)^{th}$ correction factor)/(the BNP concentration value of the $n^{th}$ standard as measured by the BNP assay to be corrected−the BNP concentration value of the $(n-1)^{th}$ standard as measured by the BNP assay to be corrected)]×(the actual measured value−the BNP concentration value of the $(n-1)^{th}$ standard as measured by the BNP assay to be corrected); and (i×[n+1]) when the actual measured value is more than the BNP concentration value of the $n^{th}$ standard as measured by the BNP assay to be corrected, a numerical value obtained by multiplying the actual measured value by the $n^{th}$ correction factor.

In an embodiment of the invention, steps (1) and (2) may correspond to step (A) and step (3) may correspond to step (B).

An embodiment of the invention may include any combination of each general embodiment and/or each specific embodiment as listed herein and in the following Examples.

EXAMPLES

Hereinbelow, the invention will be described in more detail with reference to Examples. However, the invention is not limited to these Examples.

Example 1 To Investigate Abundance Ratio of proBNP in Plasma Sample

Example 1-1

1.1.1 Assay Kit for Measuring Abundance Ratio of proBNP in Plasma Sample

Kit A, which specifically measures just proBNP but does not measure BNP-32, and kit B, which measures both BNP-32 and proBNP, were used to measure each in the same sample. In this way, the abundance ratio of proBNP in the sample was determined. Both the assay kits A and B are based on a two-step sandwich assay. A biotin-labeled capturing antibody BC203 (FERM BP-3515), which recognizes a C-terminal portion that is a common structural part between BNP-32 and proBNP, was added to a streptavidin (NACALAI TESQUE, INC.)-immobilized plate Nunc C8 MaxiSorp (Thermo Fisher Scientific, Inc., the US). The capturing antibody was so immobilized on the plate. Next, a sample was added and BNP-32 and proBNP in the sample were then captured. After washing and removal of unreacted material, an ALP-labeled antibody 18H5 (HyTest Ltd., Finland), which recognizes a portion at or near amino acid sequence 13 to 20 of proBNP, in kit A for specifically measuring just proBNP was added; and an ALP-labeled antibody KY-hBNP-II (FERM BP-2863), which recognizes an annular portion that is a common structure between BNP-32 and proBNP, in kit B for measuring both BNP-32 and proBNP was added. The ALP used was a commercially available product (Kikkoman Corporation). After washing, a luminescent substrate solution CDP/E (Applied Biosystems, Inc., the US) was added to measure a luminescence intensity. In kit A, just proBNP was quantified. In kit B, the sum value of BNP-32 and proBNP was quantified. Both the quantified values were used to determine the abundance ratio of proBNP in each plasma sample.

1.1.2 BNP Assay Kit for Measuring BNP Concentration in Plasma Sample by Immunoradiometric Assay (IRMA)

The BNP assay kit described in Non-patent Document 4 was used. This kit also uses an assay for detecting both proBNP and BNP-32. A protocol of this kit corresponds to a standard assay procedure for measuring a plasma BNP concentration. Thus, this kit was used to measure the innate plasma BNP concentration in each sample. Note that the BNP concentration value measured is expressed as a BNP-32 equivalent that is the sum value of the BNP-32 concentration and the proBNP concentration in terms of BNP-32 equivalent throughout the Examples.

1.1.3 Samples

The total 58-person-derived plasma samples used were collected from patients with heart disease and patients without heart disease.

Figure 1B:
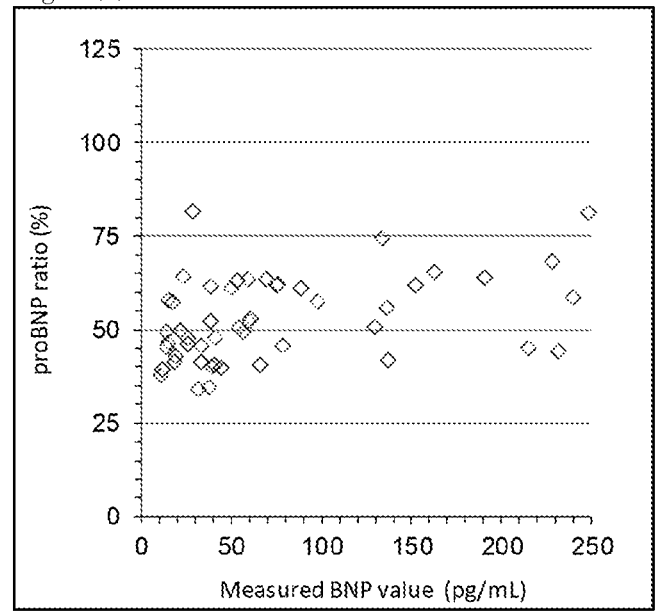
FIG. 1(b) shows the relationship between the abundance ratio of proBNP and the measured BNP concentration value in a range where the BNP concentration value measured in Example 1-1 is less than or equal to 250 pg/mL.

1.1.4 To Measure Abundance Ratio of proBNP with Respect to Plasma BNP Concentration in Plasma Sample Each plasma sample was measured using a BNP assay kit (for measuring a plasma BNP concentration) by an immunoradiometric assay in accordance with the description in Non-patent Document 4. As described in the section 1.1.1, the assay kits (kits A and B) were used to measure the abundance ratio of proBNP. FIGS. 1(a) and 1(b) show the results plotted. The abscissa represents the measured plasma BNP concentration value and the ordinate represents the abundance ratio of proBNP. The abundance ratios of proBNP in ranges of the measured plasma BNP concentration value of less than 20 pg/mL, 25 to 60 pg/mL, 75 to 150 pg/mL, 160 to 250 pg/mL, and 300 pg/mL or higher corresponded to 38% to 58% (average 47%), 34% to 81% (average 50%), 42% to 74% (average 57%), 44% to 81% (average 61%), and 62% to 78% (average 69%), respectively. There was a tendency that the abundance ratio of proBNP became higher with the increasing of the measured plasma BNP concentration value. This result has demonstrated that it is necessary to use standards with different abundance ratios of proBNP depending on the BNP concentration levels.

Example 1-2

Figure 2:
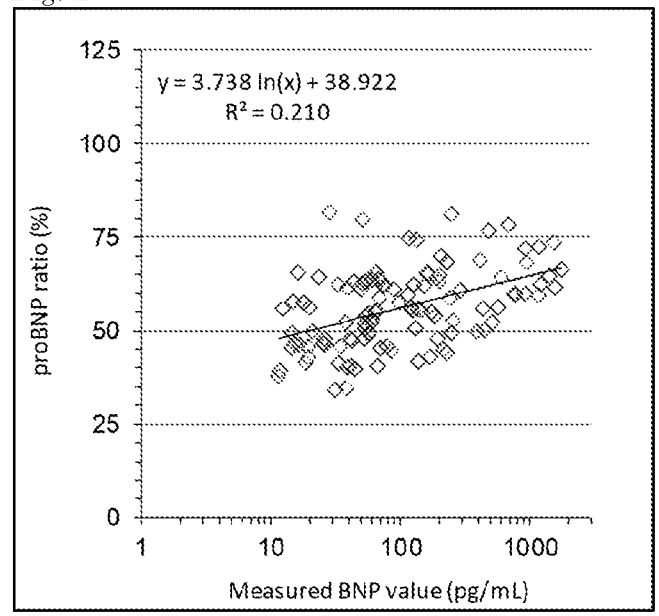
FIG. 2 shows the relationship between the abundance ratio of proBNP and the measured BNP concentration value over the entire assay range as measured in Examples 1-1 and 1-2.

Like the protocol in Example 1-1, 54-person-derived plasma samples were further collected from patients with heart disease and patients without heart disease and then each used to measure the plasma BNP concentration and the abundance ratio of proBNP. FIG. 2 shows the results plotted. The abscissa represents the measured plasma BNP concentration value of each of the total 112-person-derived samples obtained in Examples 1-1 and 1-2 and the ordinate represents the abundance ratio of proBNP. Like Example 1-1, there was a tendency that the abundance ratio of proBNP became higher with the increasing of the measured plasma BNP concentration value.

(Example 2) To Investigate Effects of Correction Using BNP Standards 2.1 Samples The total 10-person-derived plasma samples used were collected from patients with heart disease and patients without heart disease.

2.2 To Prepare Standard Set of the Invention

A standard set of the invention was prepared by removing BNP from commercially available healthy subject plasma and then adding commercially available glycosylated proBNP (HyTest Ltd., Finland) and synthetic BNP-32 (PEPTIDE INSTITUTE, INC., Japan) as follows. In a BNP assay standard for measurement in a low-concentration range (hereinafter, also referred to as a "low level standard"), the glycosylated proBNP and the BNP-32 were added into the above processed plasma such that the BNP concentration was set to 40 pg/mL (BNP-32 equivalent) and the glycosylated proBNP/BNP-32 mole ratio was set to 1/1 (the proBNP abundance ratio was 50%). In a BNP assay standard for measurement in a high-concentration range (hereinafter, also referred to as a "high level standard"), the glycosylated proBNP and the BNP-32 were added into the above processed plasma such that the BNP concentration was set to 200 pg/mL (BNP-32 equivalent) and the glycosylated proBNP/BNP-32 mole ratio was set to 3/1 (the proBNP abundance ratio was 75%). The combination of these two standards is called a standard set of the invention or the present product. The substance amounts (mol) of proBNP and BNP-32 added were determined using amino acid analysis throughout the Examples. These amounts were used to determine the BNP concentration in each standard.

2.3 To Prepare Standard Set of Conventional Art

Meanwhile, as a standard set of conventional art, each BNP assay standard for measurement in a low-concentration range (40 pg/mL BNP-32 equivalent) and each BNP assay standard for measurement in a high-concentration range (200 pg/mL BNP-32 equivalent) were prepared by adding only glycosylated proBNP, by adding only BNP-32, or by adding glycosylated proBNP and BNP-32 in a mole ratio of 1/1 (proBNP/BNP-32) into commercially available healthy subject plasma after BNP was removed.

2.4 To Measure Samples and Each Standard in Each Standard Set

The BNP concentration value measured in each plasma sample or each standard of each standard set was measured using a BNP assay kit for an immunoradiometric assay, which was a BNP standard assay procedure, as well as three different commercially available BNP assay kits: "commercially available BNP assay kit A", "commercially available BNP assay kit B", and "commercially available BNP assay kit C". These BNP assay kits were used for measurement according to the description in Non-patent Document 4 in the case of IRMA and according to the package insert in each kit in the case of the commercially available BNP assay kits. Note that the commercially available BNP assay kit A involves a chemiluminescence enzyme immunoassay (CLEIA) and the commercially available BNP assay kits B and C both involve a chemiluminescence immunoassay (CLIA). Hereinbelow, these respective three BNP assay kits may be referred to as "each BNP assay kit".

2.5 to Determine Correction Factor and to Correct Value Measured

The value measured in each standard by each BNP assay kit was compared to the value measured in the standard of the BNP assay kit by an immunoradiometric assay, which was a standard assay procedure. For each low level standard and each high level standard of each different standard set, the measured value ratio "value measured by the standard assay procedure/value measured by each BNP assay kit" was determined. Then, the ratio for each BNP assay kit was used to correct the value measured in each sample by the BNP assay kit as follows.

(i) For a sample in which the value measured in the sample (actual measured value) was less than or equal to the value measured in the low level standard by the corresponding BNP assay kit, the value measured in the sample was multiplied by the ratio determined for the low level standard.

(ii) For a sample in which the value measured in the sample was larger than the value measured in the low level standard by the corresponding BNP assay kit and less than or equal to the value measured in the high level standard by the corresponding BNP assay kit, the value measured in the sample was multiplied by a factor calculated, using the respective ratios determined for the low level standard and the high level standard, by the following formula:

$$\text{Ratio determined for the low level standard} + [(\text{Ratio determined for the high level standard} - \text{Ratio determined for the low level standard})/(\text{Value measured in the high level standard by the corresponding BNP assay kit} - \text{Value measured in the low level standard by the corresponding BNP assay kit})] \times (\text{Value measured in the sample} - \text{Value measured in the low level standard by the corresponding BNP assay kit}).$$

(iii) For a sample in which the value measured in the sample was larger than the value measured in the high level standard by the corresponding BNP assay kit, the value measured in the sample was multiplied by the ratio estimated for the high level standard.

Figure 3:
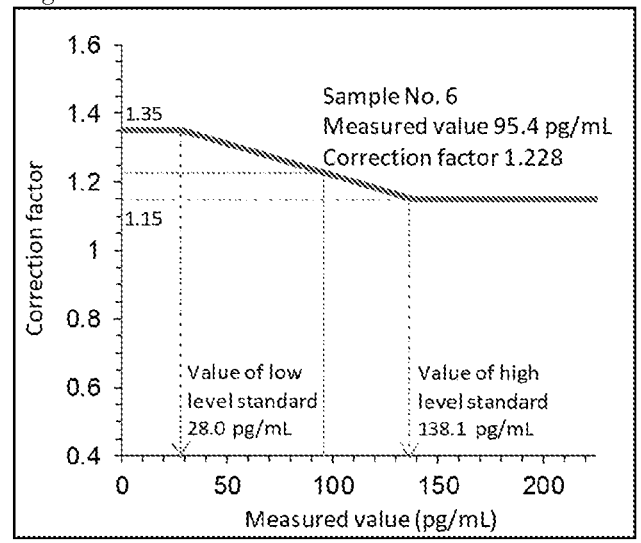
FIG. 3 shows an example of the relationship between a value measured in a sample and a correction factor applicable to a value measured using a commercially available BNP assay kit A.

FIG. 3 shows an example of how the value measured in each sample was associated with the correction factor based on the values measured in the low level standard and the high level standard of the invention by the commercially available BNP assay kit A.

2.6 Effects of Correction on Value Measured (1) Results of Measuring Plasma Samples by Each BNP Assay Kit The values measured in plasma samples and respective standards by the standard assay procedure or each BNP assay kit were as shown in Tables 1 and 2.

TABLE 1

| Sample No. | Immunoradiometric assay (Reference assay) pg/mL | Commercially available BNP assay kit A pg/mL | Commercially available BNP assay kit B pg/mL | Commercially available BNP assay kit C pg/mL |
|---|---|---|---|---|
| 1 | 22.8 | 17.4 | 24.4 | 17.7 |
| 2 | 39.9 | 31.1 | 43.5 | 28.4 |
| 3 | 57.6 | 43.8 | 62.9 | 33.6 |
| 4 | 60.2 | 62.2 | 79.1 | 52.3 |
| 5 | 91.9 | 73.1 | 99.2 | 56.7 |
| 6 | 130.9 | 95.4 | 121.0 | 79.6 |
| 7 | 145.2 | 147.4 | 165.2 | 108.6 |
| 8 | 212.9 | 178.4 | 208.7 | 128.3 |
| 9 | 351.7 | 277.6 | 345.9 | 218.3 |
| 10 | 450.5 | 359.3 | 419.7 | 310.2 |

TABLE 2

| | Standard | Immunoradiometric assay (Reference assay) pg/mL | Commercially available BNP assay kit A pg/mL | Commercially available BNP assay kit B pg/mL | Commercially available BNP assay kit C pg/mL |
|---|---|---|---|---|---|
| Invention | Low level standard (proBNP 50%) | 37.7 | 28.0 | 42.9 | 23.6 |
| | High level standard (proBNP 75%) | 158.9 | 138.1 | 156.0 | 103.3 |
| Conventional art | Low level standard (only proBNP) | 36.4 | 36.6 | 41.6 | 26.6 |
| | High level standard (only proBNP) | 181.8 | 197.5 | 164.6 | 126.8 |

TABLE 2-continued

| Standard | | Immunoradio-metric assay (Reference assay) pg/mL | Commercially available BNP assay kit A pg/mL | Commercially available BNP assay kit B pg/mL | Commercially available BNP assay kit C pg/mL |
|---|---|---|---|---|---|
| Low level standard (only BNP-32) | | 35.8 | 37.6 | 53.6 | 22.9 |
| High level standard (only BNP-32) | | 181.5 | 187.8 | 238.8 | 85.2 |
| Low level standard (proBNP/BNP-32 1:1) | | 37.8 | 36.9 | 45.9 | 22.9 |
| High level standard (proBNP/BNP-32 1:1) | | 186.0 | 203.8 | 205.4 | 108.5 |

Figure 4:
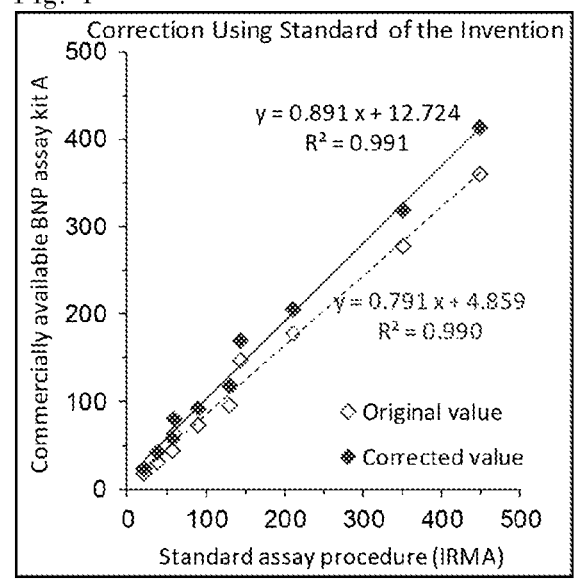
FIG. 4 illustrates how the BNP concentration value measured using a commercially available BNP assay kit A is correlated to the BNP concentration value measured by a standard assay procedure before and after correction by a correction method of the invention.
Figure 5:
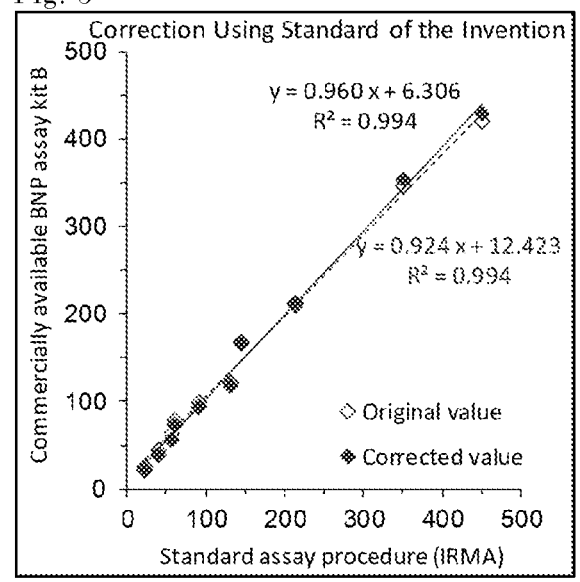
FIG. 5 illustrates how the BNP concentration value measured using a commercially available BNP assay kit B is correlated to the BNP concentration value measured by a standard assay procedure before and after correction by a correction method of the invention.
Figure 6:
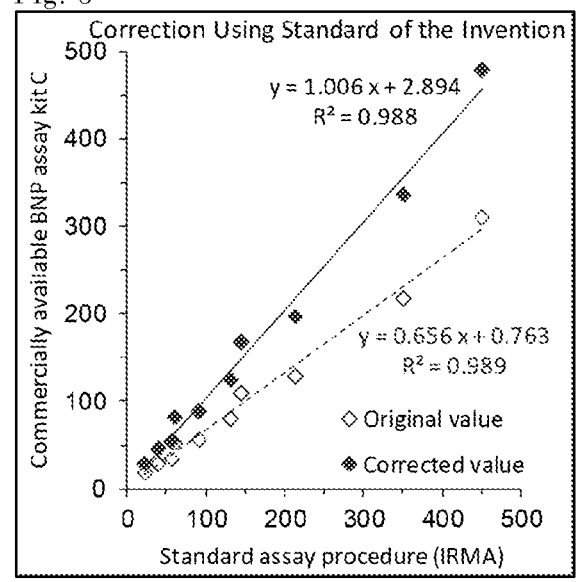
FIG. 6 illustrates how the BNP concentration value measured using a commercially available BNP assay kit C is correlated to the BNP concentration value measured by a standard assay procedure before and after correction by a correction method of the invention.

The values measured in plasma samples by each BNP assay kit were correlated to the values measured in the plasma samples by the standard assay procedure as follows:

for the commercially available BNP assay kit A, $y=0.791x+4.859$ (FIG. 4);

for the commercially available BNP assay kit B, $y=0.924x+12.423$ (FIG. 5); and for the commercially available BNP assay kit C, $y=0.656x+0.763$ (FIG. 6).

The average slope of these three correlation equations was 0.790 and the coefficient of variation (CV %) was 17.0%. Note that the correlation in each BNP assay kit was each determined throughout the Examples by a least-squares method using a primary regression line.

(2) To Determine Correction Factor for Each Standard of the Invention

Table 3 shows the correction factors each determined by dividing the value measured in each standard of the invention by the standard assay procedure by the value measured in the standard by each BNP assay kit.

TABLE 3

| Standard | Measured value by Immunoradio-metric assay (pg/mL) | Commercially available BNP assay kit A Correction factor | Commercially available BNP assay kit B Correction factor | Commercially available BNP assay kit C Correction factor |
|---|---|---|---|---|
| Low level standard (proBNP 50%) | 37.7 | 1.35 | 0.88 | 1.60 |
| High level standard (proBNP 75%) | 158.9 | 1.15 | 1.02 | 1.54 |

(3) To Correct, Using Correction Method of the Invention, Value Measured by Each BNP Assay Kit According to the correction method indicated in the section 2.5, the values measured in plasma samples by each BNP assay kit were corrected. As a result, the values measured in the plasma samples by each BNP assay kit were correlated to the values measured in the plasma samples by the standard assay procedure as follows:

for the commercially available BNP assay kit A, $y=0.891x+12.724$ (FIG. 4);

for the commercially available BNP assay kit B, $y=0.960x+6.306$ (FIG. 5); and for the commercially available BNP assay kit C, $y=1.006x+2.894$ (FIG. 6).

Figure 7:
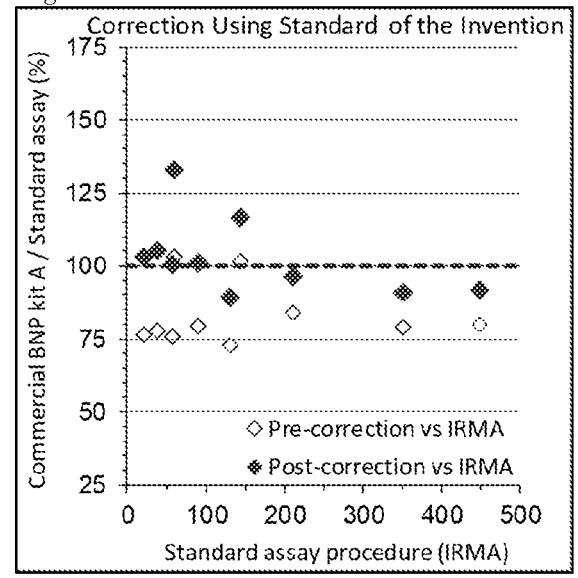
FIG. 7 shows the percentage of the BNP concentration value measured using a commercially available BNP assay kit A before and after correction by a correction method of the invention with respect to the BNP concentration value measured by a standard assay procedure.
Figure 8:
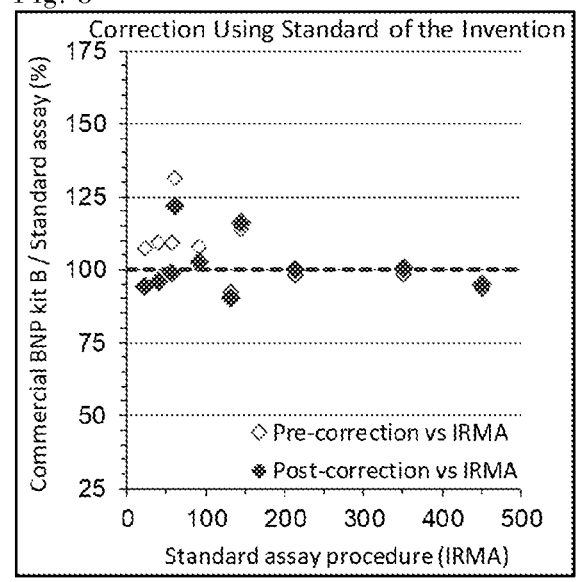
FIG. 8 shows the percentage of the BNP concentration value measured using a commercially available BNP assay kit B before and after correction by a correction method of the invention with respect to the BNP concentration value measured by a standard assay procedure.
Figure 9:
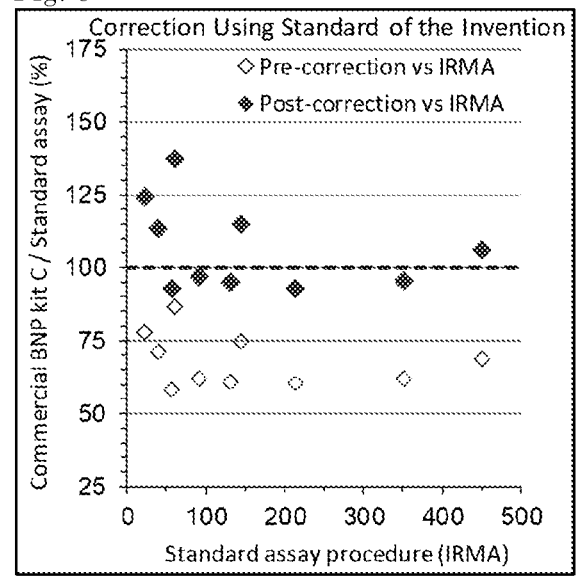
FIG. 9 shows the percentage of the BNP concentration value measured using a commercially available BNP assay kit C before and after correction by a correction method of the invention with respect to the BNP concentration value measured by a standard assay procedure.

The average slope of these three correlation equations was 0.952, which slope was closer to 1 than before the correction. The coefficient of variation was 6.1%, which was 36% of the value (17.0%) before the correction. Accordingly, the difference in slope among the respective BNP assay kits became small. In view of the above, it is understandable that the correction method of the invention makes much smaller the deviation in the values measured between the respective BNP assay kits. Further, the ratio of the individual BNP concentration values measured by each BNP assay kit and then corrected with respect to those measured by the standard assay procedure was closer to 100% (FIGS. 7 to 9).

FIGS. 4 to 6 show graphs illustrating how each BNP assay kit is correlated to the standard assay procedure between before and after the correction. In addition, FIGS. 7 to 9 show graphs illustrating the percentages of the BNP concentration values measured by each BNP assay kit before or after the correction with respect to those measured by the standard assay procedure. In FIGS. 4 to 9, the abscissa represents the BNP concentration value measured by the standard assay procedure. In addition, in FIGS. 4 to 6, the ordinate represents the BNP concentration value measured by each BNP assay kit. In FIGS. 7 to 9, the ordinate represents the percentage of the BNP concentration value measured by each BNP assay kit with respect to that measured by the standard assay procedure. Each open diamond-shaped symbole denotes a value before correction and each closed diamond-shaped symbol denotes a value after correction.

(4) Comparative Example of BNP Standard of Conventional Art

Meanwhile, Table 4 shows the correction factors each determined by dividing the value measured in each standard of conventional art by the standard assay procedure by the value measured in the standard by each BNP assay kit.

TABLE 4

| Standard | Measured value by Immunoradiometric assay (pg/mL) | Commercially available BNP assay kit A Correction factor | Commercially available BNP assay kit B Correction factor | Commercially available BNP assay kit C Correction factor |
|---|---|---|---|---|
| Low level standard (only proBNP) | 36.4 | 0.99 | 0.88 | 1.37 |
| High level standard (only proBNP) | 181.8 | 0.92 | 1.10 | 1.43 |
| Low level standard (only BNP-32) | 35.8 | 0.95 | 0.67 | 1.56 |
| High level standard (only BNP-32) | 181.5 | 0.97 | 0.76 | 2.13 |
| Low level standard (proBNP/BNP-32 1:1) | 37.8 | 1.02 | 0.82 | 1.65 |
| High level standard (proBNP/BNP-32 1:1) | 186.0 | 0.91 | 0.91 | 1.71 |

Like the correction using a standard set of the invention, the value measured in each standard of conventional art was used to correct the values measured in plasma samples by each BNP assay kit. The results are as shown below.

Figure 10:
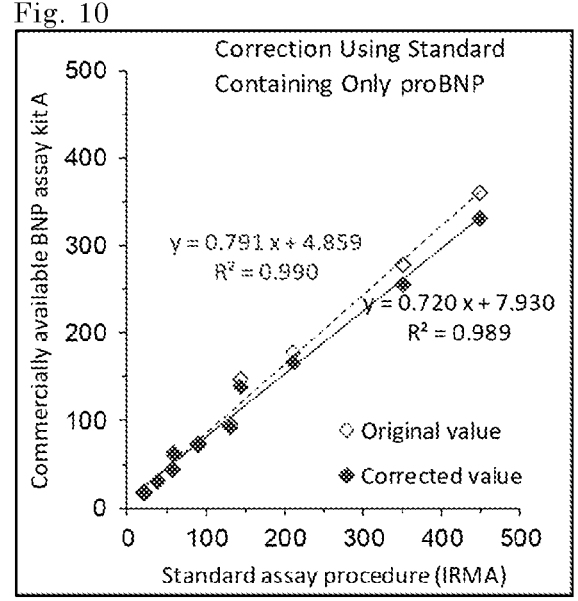
FIG. 10 illustrates how the BNP concentration value measured using a commercially available BNP assay kit A is correlated to the BNP concentration value measured by a standard assay procedure before and after correction using standards containing only proBNP for both low and high levels.
Figure 11:
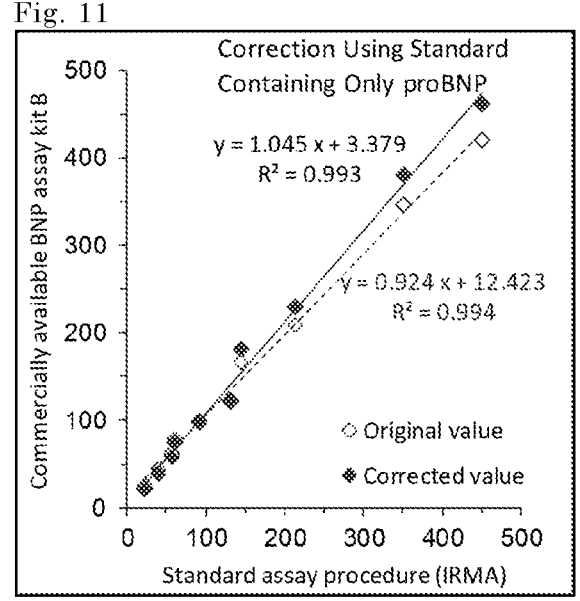
FIG. 11 illustrates how the BNP concentration value measured using a commercially available BNP assay kit B is correlated to the BNP concentration value measured by a standard assay procedure before and after correction using standards containing only proBNP for both low and high levels.
Figure 12:
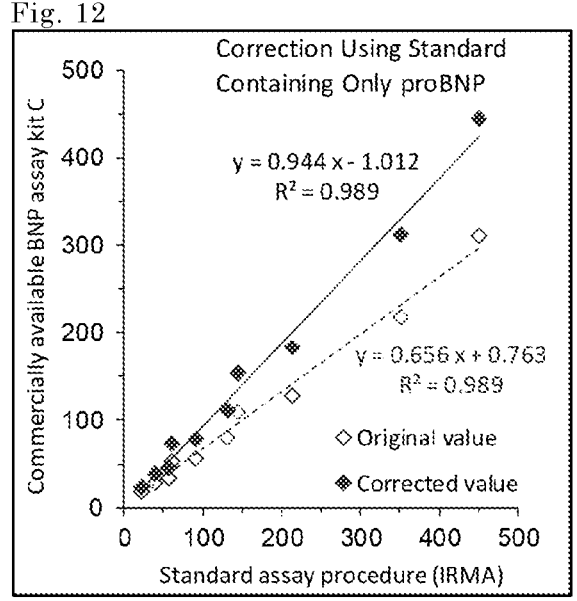
FIG. 12 illustrates how the BNP concentration value measured using a commercially available BNP assay kit C is correlated to the BNP concentration value measured by a standard assay procedure before and after correction using standards containing only proBNP for either low and high levels.

(i) When a standard containing only glycosylated proBNP was used for correction, the values measured in the plasma samples by each BNP assay kit were correlated to the values measured in the plasma samples by the standard assay procedure as follows:

for the commercially available BNP assay kit A, y=0.720x+7.930 (FIG. 10);

for the commercially available BNP assay kit B, y=1.045x+3.379 (FIG. 11); and for the commercially available BNP assay kit C, y=0.944x−1.012 (FIG. 12).

Figure 19:
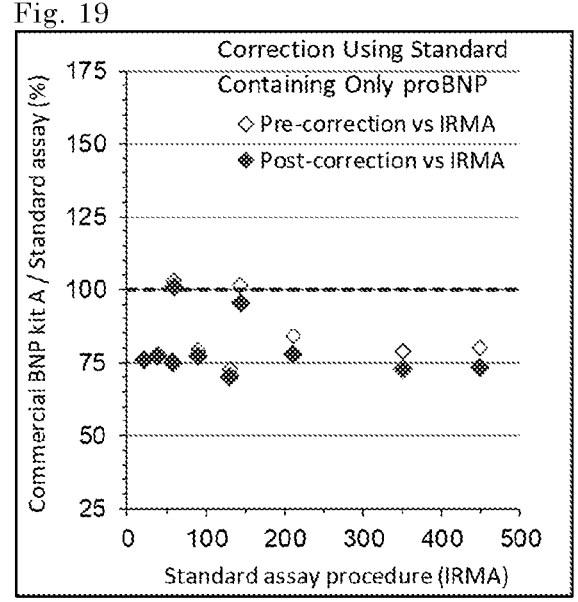
FIG. 19 shows the percentage of the BNP concentration value measured using a commercially available BNP assay kit A before and after correction using standards containing only proBNP for both low or high levels with respect to the BNP concentration value measured by a standard assay procedure.
Figure 20:
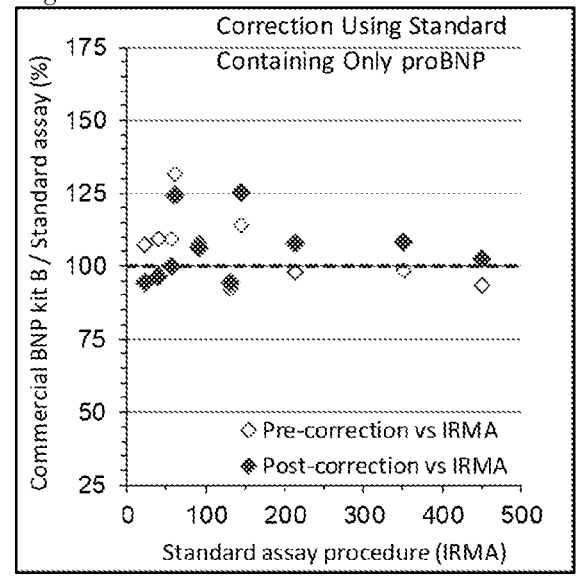
FIG. 20 shows the percentage of the BNP concentration value measured using a commercially available BNP assay kit B before and after correction using standards containing only proBNP for both low and high levels with respect to the BNP concentration value measured by a standard assay procedure.
Figure 21:
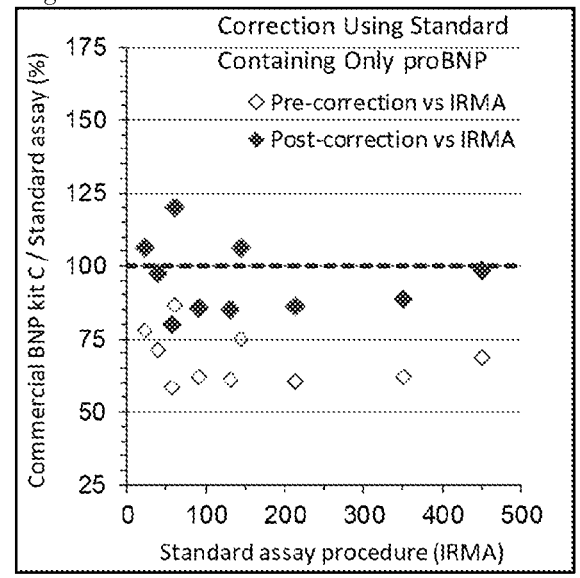
FIG. 21 shows the percentage of the BNP concentration value measured using a commercially available BNP assay kit C before and after correction using standards containing only proBNP for both low and high levels with respect to the BNP concentration value measured by a standard assay procedure.

The average slope of these three correlation equations was 0.903 and the coefficient of variation was 18.4%, which was about 3.0 times larger than the coefficient of variation (6.1%) after the correction by the correction method of the invention. In addition, the ratio of the individual BNP concentration values measured by each BNP assay kit and then corrected with respect to those measured by the standard assay procedure was in turn found to deviate from 100% in some samples by the correction (FIGS. 19 to 21).

Figure 13:
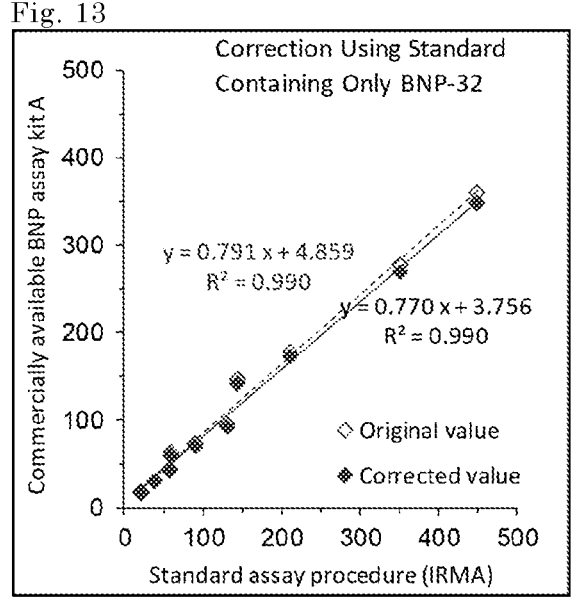
FIG. 13 illustrates how the BNP concentration value measured using a commercially available BNP assay kit A is correlated to the BNP concentration value measured by a standard assay procedure before and after correction using standards containing only BNP-32 for both low and high levels.
Figure 14:
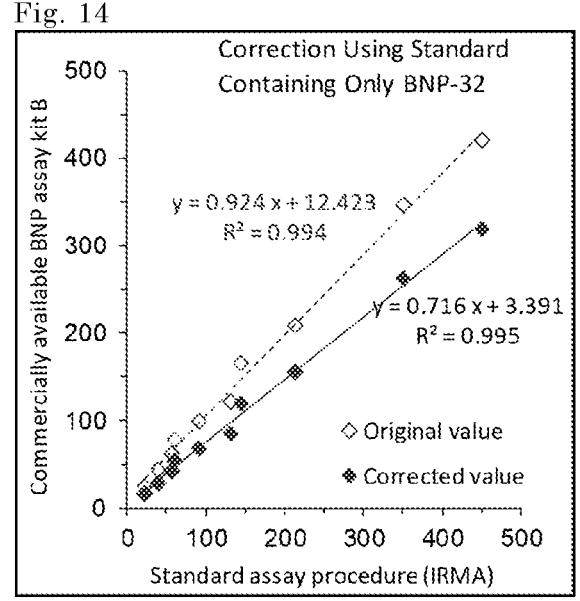
FIG. 14 illustrates how the BNP concentration value measured using a commercially available BNP assay kit B is correlated to the BNP concentration value measured by a standard assay procedure before and after correction using standards containing only BNP-32 for both low and high levels.
Figure 15:
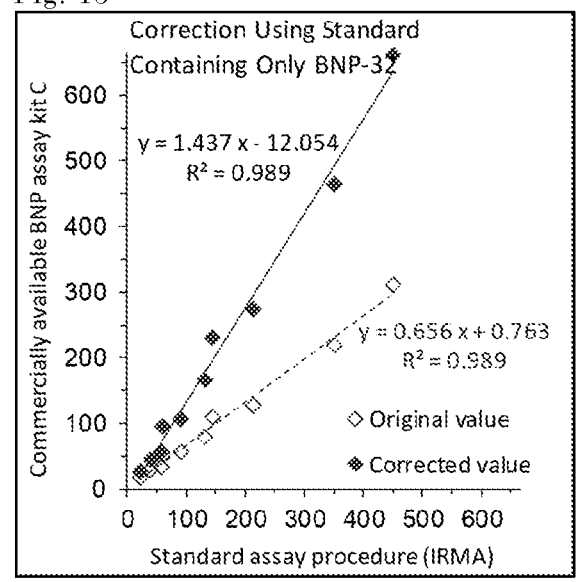
FIG. 15 illustrates how the BNP concentration value measured using a commercially available BNP assay kit C is correlated to the BNP concentration value measured by a standard assay procedure before and after correction using standards containing only BNP-32 for both low and high levels.

(ii) When a standard containing only BNP-32 was used for correction, the values measured in plasma samples by each BNP assay kit were correlated to the values measured in the plasma samples by the standard assay procedure as follows:

for the commercially available BNP assay kit A, y=0.770x+3.756 (FIG. 13);

for the commercially available BNP assay kit B, y=0.716x+3.391 (FIG. 14); and for the commercially available BNP assay kit C, y=1.437x−12.054 (FIG. 15).

The average slope of these three correlation equations was 0.974 and the coefficient of variation was 41.2%, which was about 6.8 times larger than the coefficient of variation (6.1%) after the correction by the correction method of the invention.

Figure 16:
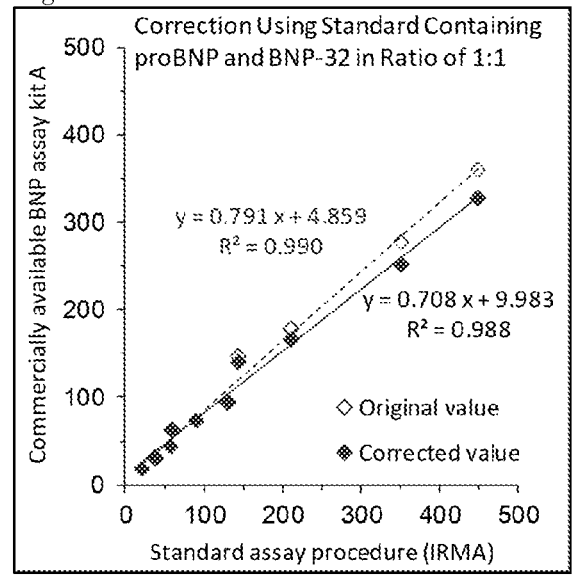
FIG. 16 illustrates how the BNP concentration value measured using a commercially available BNP assay kit A is correlated to the BNP concentration value measured by a standard assay procedure before and after correction using standards containing proBNP and BNP-32 in a ratio (proBNP/BNP-32) of 1/1 is used for both low and high levels.
Figure 17:
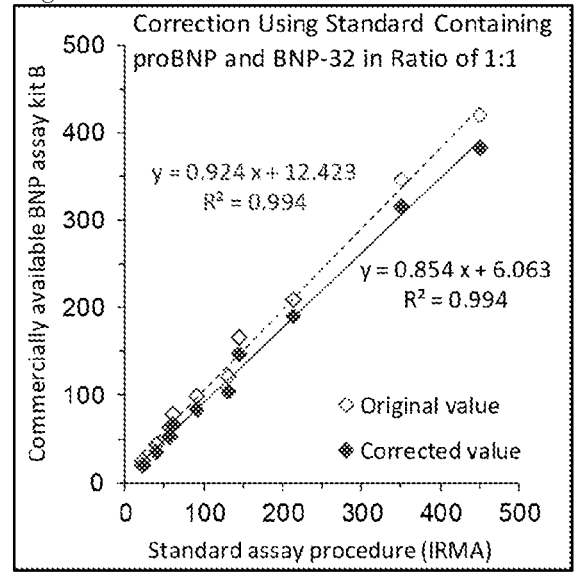
FIG. 17 illustrates how the BNP concentration value measured using a commercially available BNP assay kit B is correlated to the BNP concentration value measured by a standard assay procedure before and after correction using standards containing proBNP and BNP-32 in a ratio (proBNP/BNP-32) of 1/1 for both low and high levels.
Figure 18:
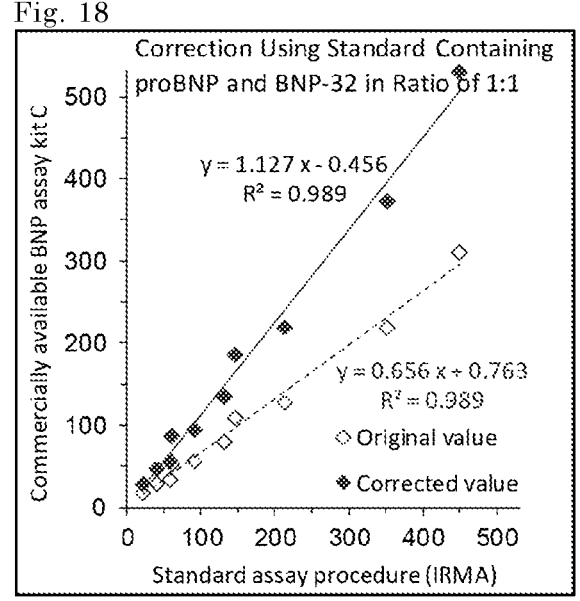
FIG. 18 illustrates how the BNP concentration value measured using a commercially available BNP assay kit C is correlated to the BNP concentration value measured by a standard assay procedure before and after correction using standards containing proBNP and BNP-32 in a ratio (proBNP/BNP-32) of 1/1 for both low and high levels.

(iii) When both a low level standard and a high level standard containing glycosylated proBNP and BNP-32 in a ratio of 1/1 (proBNP/BNP-32) were used for correction, the values measured in plasma samples by each BNP assay kit were correlated to the values measured in the plasma samples by the standard assay procedure as follows:

for the commercially available BNP assay kit A, y=0.708x+9.983 (FIG. 16);

for the commercially available BNP assay kit B, y=0.854x+6.063 (FIG. 17); and for the commercially available BNP assay kit C, y=1.127x−0.456 (FIG. 18).

The average slope of these three correlation equations was 0.895 and the coefficient of variation was 23.7%, which was about 3.9 times larger than the coefficient of variation (6.1%) after the correction by the correction method of the invention.

FIGS. 10 to 18 show graphs illustrating how each BNP assay kit is correlated to the standard assay procedure when the standard set of each of the above (i), (ii), or (iii) was used for correction. In addition, FIGS. 19 to 21 show graphs illustrating the percentage of each BNP concentration value measured by each BNP assay kit using the above standard set (i) before or after the correction, the effects of which were found to be closest to those of the correction in the invention, with respect to that measured by the standard assay procedure. In FIGS. 10 to 21, the abscissa represents the value measured by the standard assay procedure. In addition, in FIGS. 10 to 18, the ordinate represents the value measured by each BNP assay kit. In FIGS. 19 to 21, the ordinate represents the percentage of each BNP concentration value measured by each BNP assay kit with respect to that measured by the standard assay procedure. Each open diamond-shaped symbol denotes a value before correction and each closed diamond-shaped symbol denotes a value after correction.

Collectively, after the correction of conventional art, the values measured by each BNP assay kit deviated three times or more from those obtained after correction by a correction method of the invention when the deviation was expressed as the coefficient of variation in the slope of correlation equation.

INDUSTRIAL APPLICABILITY

A BNP assay standard set comprising a plurality of standards, each containing BNP-32 and proBNP may be used to correct BNP concentration values measured using different BNP assay kits. In this case, the post-correction measured values can be matched better among these BNP assay kits than the case of correcting the BNP concentration values measured by these BNP assay kits using a conventional BNP assay standard set.

The invention claimed is:

1. A BNP assay standard set comprising a plurality of standards, each containing BNP-32 and proBNP, wherein BNP-32/proBNP (a mole ratio) differs among the standards; and when the standard at a high mole ratio and the standard at a low mole ratio are compared with each other, the standard at a high mole ratio has a lower BNP concentration that is the sum value of BNP-32 and proBNP concentrations than the standard at a low mole ratio.

2. The BNP assay standard set according to claim 1, wherein the set comprises at least two standards, wherein the mole ratio (BNP-32/proBNP) of a first standard is from 40/60 to 60/40, and the mole ratio (BNP-32/proBNP) of a second standard is from 15/85 to 35/65.

3. The BNP assay standard set according to claim 2, wherein the first standard has a BNP concentration of from 20 to 75 pg/mL and the second standard has a BNP concentration of from 150 to 300 pg/mL.

4. A BNP assay kit comprising the BNP assay standard set according to claim 1.

5. A BNP assay kit comprising information about a correction factor determined using the BNP assay standard set according to claim 1.

6. A BNP assay kit comprising the BNP assay standard set according to claim 2.

SEQUENCE LISTING

```
<160> NUMBER OF SEQ ID NOS: 2

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
                100                 105

<210> SEQ ID NO 2
<211> LENGTH: 32
<212> TYPE: PRT
<213> ORGANISM: Homo sapiens

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30
```

7. A BNP assay kit comprising the BNP assay standard set according to claim 3.

\* \* \* \* \*